US006580943B2

United States Patent
Nissilä

(10) Patent No.: US 6,580,943 B2
(45) Date of Patent: Jun. 17, 2003

(54) ECG ELECTRODE STRUCTURE AND METHOD FOR MEASURING ECG SIGNAL FROM A PERSON IN WATER

(75) Inventor: Seppo Nissilä, Oulu (FI)

(73) Assignee: Polar Electro Oy, Kempele (FI)

( * ) Notice: Subject to any disclaimer, the term of this patent is extended or adjusted under 35 U.S.C. 154(b) by 42 days.

(21) Appl. No.: 09/885,872

(22) Filed: Jun. 20, 2001

(65) Prior Publication Data

US 2002/0007126 A1 Jan. 17, 2002

(30) Foreign Application Priority Data

Jun. 29, 2000 (FI) ............................................. 20001543

(51) Int. Cl.[7] .......................................... A61B 5/0402
(52) U.S. Cl. ...................................... 600/509; 600/372
(58) Field of Search ........................ 600/372, 382–394, 600/509

(56) References Cited

U.S. PATENT DOCUMENTS

| 4,625,733 A | 12/1986 | Säynäjäkangas |
| 4,637,399 A | 1/1987 | Asai et al. |
| 4,681,118 A | 7/1987 | Asai et al. |
| 4,791,933 A | 12/1988 | Asai et al. |
| 4,899,753 A | 2/1990 | Inoue et al. |
| 5,197,479 A | 3/1993 | Hubelbank et al. |

FOREIGN PATENT DOCUMENTS

| EP | 0612498 A1 | 8/1994 |
| EP | 0784960 A1 | 7/1997 |
| FR | 2 655 834 | 6/1991 |
| WO | WO99/56613 | 11/1999 |

OTHER PUBLICATIONS

Bronzino, Joseph D., *The Biomedical Engineering Handbook* (1995) pp. 1185–1190.
Guyton, Arthur C., *Human Physiology and Mechanisms of Disease* (1982) pp. 128–133.

*Primary Examiner*—Scott M. Getzow
(74) *Attorney, Agent, or Firm*—Hoffman & Baron, LLP

(57) ABSTRACT

The invention relates to an ECG electrode structure suitable for use in water during swimming, for example, and to a method for measuring an ECG signal from a person who is in water. To measure a difference in potential (304), the ECG electrode structure comprises a first measurement electrode (502) arranged to be in contact with an area of the skin (202) on a user's body such that, when in use, the electrode is electrically insulted (510) from the water (108), and a second measurement electrode (300). When in use, the second measurement electrode (300) is arranged to be in contact only with the water (108), the second measurement electrode (300) thus being in contact through the water with an area of the person's body other than the area under the first measurement electrode (502).

25 Claims, 3 Drawing Sheets

ECG ELECTRODE STRUCTURE AND METHOD FOR MEASURING ECG SIGNAL FROM A PERSON IN WATER

FIELD OF THE INVENTION

The invention relates to an ECG electrode structure suitable to be used in water during swimming, for example, and to a method for measuring an ECG signal from a person who is in water.

BRIEF DESCRIPTION OF THE RELATED ART

Heart rate measurement is based on monitoring the operation of the heart. When heart contracts, it causes a series of electric pulses in the body that can be measured. The measurement and analysis of a signal thus caused is known as electrocardiography (ECG). The signal itself is called an ECG signal. Further details about ECG can be obtained from Guyton, Arthur C.: *Human Physiology and Mechanisms of Disease, Third edition, W. B. Saunders Company* 1982, *ISBN 4-7557-0072-8*, Chapter 13: *The Electrocardiogram,* which is included herein by reference.

U.S. Pat. No. 4,625,733, Säynäjäkangas, teaches a wireless and continuous heart rate measurement concept consisting of a measuring belt to be positioned on the chest by means of an elastic band and a heart rate receiver worn on the wrist like a watch.

The measuring belt consists of a bending piece attached to the chest with an elastic belt, the piece comprising two measurement electrodes that set against the skin and an ECG detection block connected to the measurement electrodes for generating heart rate information based on the ECG signal measurements made by the measurement electrodes. The transmitter on the measuring belt uses inductive telemetry to transmit the heart rate information to a heart rate receiver attached to the user's wrist.

The measurement electrodes detect a projection of the heart's electric field on the skin. Although both the electrodes are measurement electrodes by structure, the electrode which is on the left-hand side of the measuring belt and partly sets on the heart is usually the actual measurement electrode and the right-hand side electrode is a reference or ground electrode. The measurement is carried out for measuring a difference in potential, i.e. voltage, between the measurement electrodes in question. From the point of view of the measurement, the only important aspect is the potential difference between the first and the second electrode.

Further details about the electronics needed in the measurement can be obtained from Bronzino, Joseph D.: *The Biomedical Engineering Handbook*, CRC Press 1995, Chapter 72: *Biopotential Amplifiers* which is included herein by reference.

In order for the described measurement electrode structure to be applicable also during swimming, the measurement electrodes must be insulated from water. The insulation can be carried out by arranging a protrusion around the measurement electrodes to prevent water from entering between the measurement electrode and the skin when the belt is placed against the skin. However, this is not a particularly good solution because when the swimmer jumps into water or during swimming, the movement of the muscles causes the belt to move whereby water gets between the measurement electrode and the skin. In addition, movement of the chest caused by breathing may cause the belt to move.

In a way, water can be considered to serve as a third electrode because, except for the body areas that are under the measurement electrodes, the body is in contact with the water which is usually conductive due to the impurities it contains. If both the measurement electrodes in the measurement belt get into contact with the water, the measurement electrodes are, in an electric sense, shortcut with respect to each other and the potential difference between them can no longer be measured. If only the first one of the measurement electrodes in the measuring belt gets into contact with water, then the potential difference between the electrode consisting of the first measurement electrode and the water and the second measurement electrode is measured. When the first measurement electrode changes to an electrode consisting of the first measurement electrode and the water, the projection of the heart's electric field changes, thereby interfering with the measurement accuracy.

The electrodes can also be attached using adhesive tape or glue, but they are not very pleasant to use. In addition, glue may soil the water.

U.S. Pat. Nos. 4,637,399 and 4,791,933 describe electrode structures to be attached to the surface of the skin in a waterproof manner. The fastening is based on the use of a suction disc. The solution is not very pleasant to use, because the suction disc causes a negative pressure which draws the skin to it, thereby possibly causing redness of the skin.

SUMMARY OF THE INVENTION

It is an object of the invention to provide an improved ECG electrode structure and an improved method for measuring an ECG signal from a person who is in water. One aspect of the invention is an ECG electrode structure according to claim 1. Another aspect of the invention is a method according to claim 16 for measuring an ECG signal from a person who is in water. Other preferred embodiments of the invention are disclosed in the dependent claims.

An underlying idea of the invention is that, unlike in the prior art, the second measurement electrode is arranged to be in contact only with the water and not with the skin. Since this solution requires only one measurement electrode which is electrically insulated from water, the positioning of the electrode and its insulation are easier to carry out than in a solution where two measurement electrodes are to be positioned on the skin. This improves the reliability of the measurement.

BRIEF DESCRIPTION OF THE DRAWINGS

In the following, the preferred embodiments of the invention will be described of example with reference to the accompanying drawings, in which.

DETAILED DESCRIPTION OF THE PREFERED EMBODIMENTS

Figure 1:
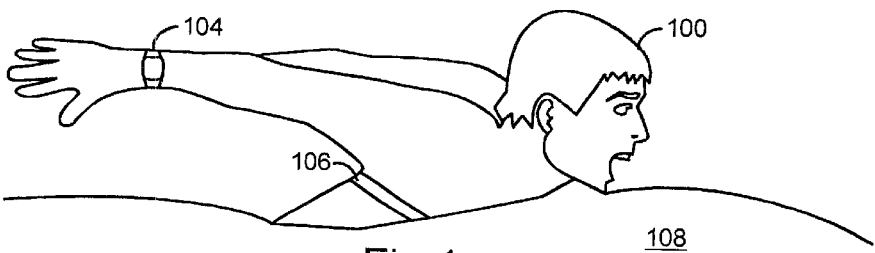
FIG. 1 illustrates swimming exercise in which a heart rate monitor is used.

FIG. 1 shows a swimmer 100 using a heart rate monitor 104 in water 108 with an electrode transmitter belt 106 arranged around his chest to measure his heart rate. As already stated, jumping in the water or contraction of the back and chest muscles during swimming may cause the electrode belt 106 to move, whereby water entering between the measurement electrodes and the skin may interfere with the measurement.

In the following, the electrode transmitter belt 106 of the heart rate monitor will be described in greater detail with reference to FIG. 5. The electrode belt 106 comprises holes 506, 508 to which an elastic band fastening the electrode belt 106 around the chest is secured, usually with a male/female-type joint. Electrodes 502, 504 measuring the heart rate are connected with wires or conductive plastic to an electronics unit 500 where an ECG signal obtained from the electrodes 502, 504 is processed and transmitted to the heart rate monitor 104 carried on the wrist. As already stated, the measurement electrodes are usually positioned such that the electrode on the left-hand side which comes on the person's heart is a measurement electrode 502, and the electrode on the right-hand side is a reference electrode 504. The measurement electrode 502 is electrically insulated from the water with a relatively low ridge 510, for example. Correspondingly, the reference electrode 504 is electrically insulated from the water with a ridge 512.

Figures 5, 6:
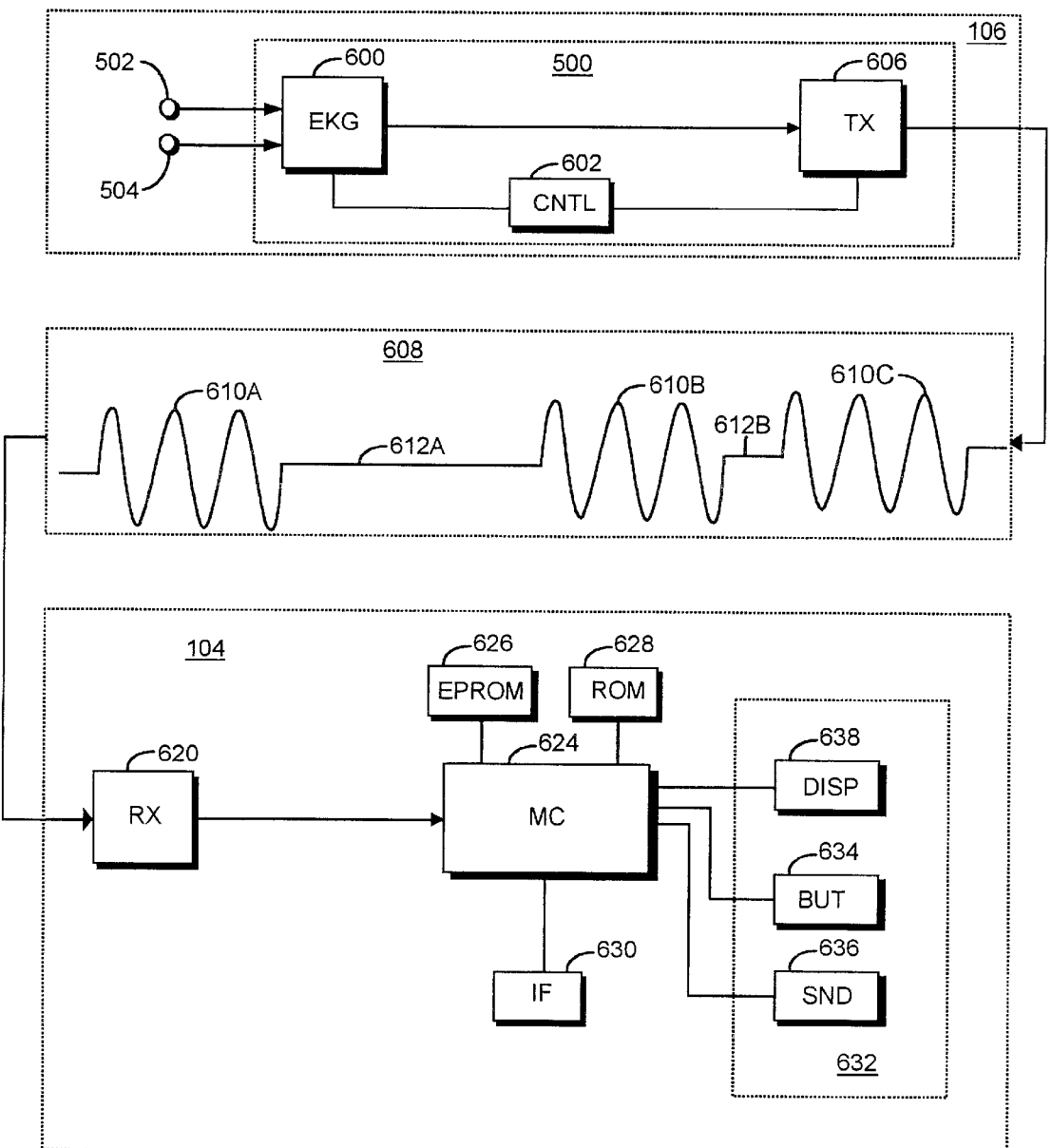
FIG. 5 illustrates an electrode transmitter belt of a heart rate monitor.
FIG. 6 illustrates the structure of a heart rate monitor transmitter belt attached to the chest, and that of a wrist-worn heart rate monitor.

FIG. 6 illustrates the structure of the transmitter electrode belt 106 and that of the heart rate monitor 104 carried on the wrist. 'Heart rate monitor' refers here to the entity formed by the transmitter electrode belt 106 and the receiver 104. It is apparent to a person skilled in the art that the electrode belt 106 and the receiver 104 may also comprise other parts than those shown in FIG. 6, although it is not relevant to describe them herein. FIG. 6 shows the essential parts of the transmitter electrode belt 106 on the top, a sample of heart rate information 608 to be transmitted in the middle, and the heart rate monitor 104 at the bottom. The electronics unit 500 of the transmitter electrode belt 106 receives heart rate information from the electrodes 502, 504 used for measuring an ECG signal. The ECG signals are preferably processed, i.e. filtered, amplified and detected, in an ECG detection block 600 using prior art methods to allow heart rate information, such as heartbeats, to be detected. To detect the heartbeat, the ECG detection block 600 measures a difference in potential between the measurement electrodes 502, 504. The detection of heart rate is based on a QRS complex detected in the heartbeat signal, for example, the letters Q, R and S referring to potential phases caused in an electric signal by an electric activation. QRS may be detected using a matched filter, whereby a model complex is compared with a measured QRS complex and when the comparison exceeds a predetermined threshold value, the complex is accepted as a heartbeat. The transmitter 606 is preferably implemented using a coil which transmits the heart rate information 608 inductively to the receiver 200 of the heart rate monitor 104 on the wrist.

One heartbeat is represented for example by one 5 kHz burst 610A or a group 610A, 610B, 610C of several bursts. Intervals 612A, 612B between the bursts 610A, 610B, 610C may be of an equal duration, or their duration may vary. The information may be transmitted inductively, or, alternatively, it may be sent optically or through a wire, for example, or using some other, wireless data transfer carried out electronically and/or magnetically. The receiver 620 comprises a receiver coil from which the received signal is transmitted through a signal receiver to control electronics 624 which control and coordinate the operation of the different parts of the heart rate monitor 104. The heart rate monitor 104 preferably also comprises memory (EPROM=Erasable Programmable Read Only Memory) 626 for storing heart rate information, and memory (ROM=Read Only Memory) 628 for storing the computer software of the heart rate monitor 104. The control electronics 624 and its memory are preferably implemented using a general-purpose microprocessor provided with the necessary system and application software, although diverse hardware implementations are also possible, such as a circuit built of separate logic components, or one or more ASICs (Application Specific Integrated Circuit). Matters affecting the solution adopted for implementing the control electronics 624 include at least requirements set to the size and energy consumption of the device, its manufacturing costs and the production volumes.

The heart rate monitor 104 often comprises an interface 630 between the heart rate monitor 104 and the external world. Through the interface 630, information stored in the heart rate monitor can be transferred for further processing to a personal computer, for example. In addition, the interface 630 can be used for updating the software of the heart rate monitor. For this purpose, special mechanisms are needed. For example, the ROM memory 628 in which the software is stored must be changed to a memory type capable of receiving writing as well, such as EEPROM (Electrically Erasable Programmable Read Only Memory).

The user interface 632 of the heart rate monitor comprises a display 638, push-buttons and/or turn-buttons 634 for making choices and for activating and stopping functions, as well as means 636 for producing sound, such as sound signals. Sound signals can also be used for example for giving an alarm if a variable to be measured is below or above control limits, or to provide other information of interest to the user.

Both the transmitter belt 106 and the heart rate monitor 104 comprise a power source, not shown in FIG. 6. The power source of the transmitter belt 106 is usually provided by means of batteries. The heart rate monitor 104 may employ a battery or other prior art means of generating power, for example a solar cell producing current from a light source, or a generator producing current from movement.

Figure 2:
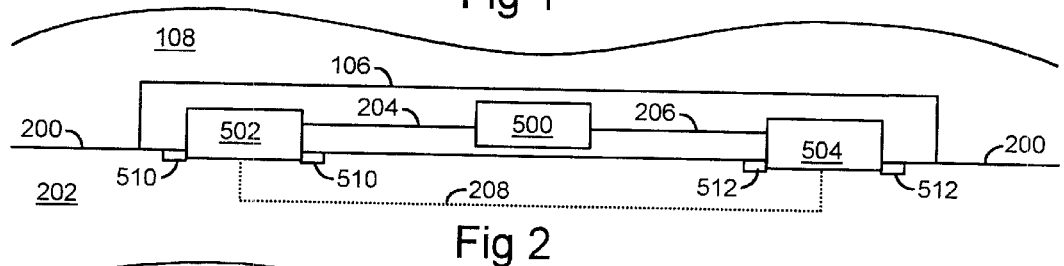
FIG. 2 illustrates measurement connections in a prior art ECG electrode structure.

FIG. 2 shows measurement connections of a prior art ECG electrode structure. The measurement electrodes 502, 504 are connected to an electronics unit 500 using wires 204, 206 or conductive plastic, for example. The electronics unit 500 measures the potential difference, i.e. voltage 208, between the measurement electrodes 502, 504. If, despite insulations 510, 512, water 108 gets between the surface 200 of the skin 202 and one or both of the electrodes 502, 504, there will be problems, as described above, in the measurement of the potential difference 208.

Figure 3:
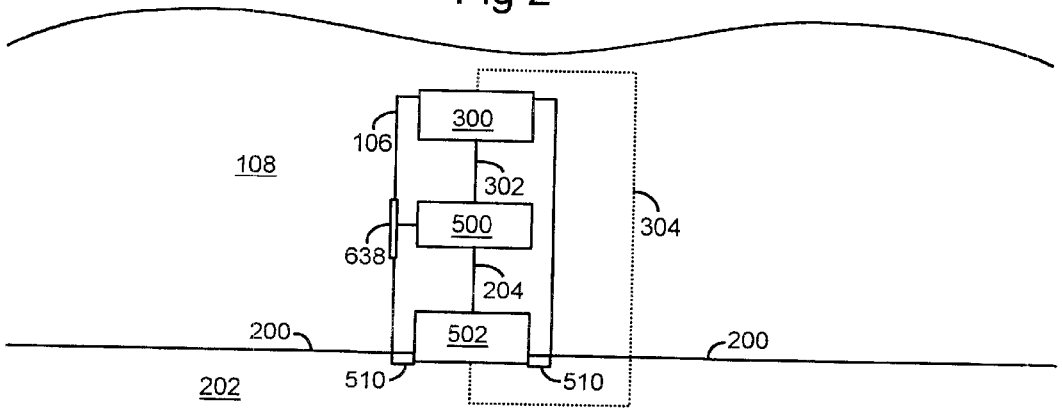
FIG. 3 illustrates a first preferred embodiment of an ECG electrode structure and measurement connections thereof.

FIG. 3 illustrates a first embodiment of the ECG electrode structure. Similarly to the prior art, the structure comprises a first measurement electrode 502 for measuring a potential difference 304, the electrode being arranged to be in contact with an area of the skin 202 on the user's body such that, when in use, the electrode is electrically insulated 510 from the water 108, and a second measurement electrode 300. When in use, the second measurement electrode 300 is arranged to be only in contact with the water 108, the electrode being in contact through the water with an area of the user's body other than the area under the first measurement electrode 502. The second measurement electrode 300 and the user's skin 202 that is not under the first measurement electrode 502 and an electric insulation 510, if any, thus form a common reference/ground potential.

Consequently, only one measurement electrode electrically insulated 510 from the water is needed, i.e. the first measurement electrode 502, the electrical insulation from the water 108 of which can be more easily and better accomplished than electrical insulation of two measurement electrodes from the water 108. Instead of a ridge 510 made of material that does not conduct electricity, the insulation can be carried out in any prior art manner, using a silicon sealing ring, for example.

The first embodiment can preferably be implemented such that the first measurement electrode 502 and the second measurement electrode 300 on the cover encapsulating the electrode structure are arranged on cover surface sides facing away from each other. Inside the cover encapsulating the ECG electrode structure can be arranged the ECG detection block 600 for producing heart rate information on the basis of the ECG signal measurements carried out by the measurement electrodes 300, 502. In addition, the transmitter 606 can be placed inside the cover encapsulating the ECG electrode structure. This allows to produce a capsule of small dimensions which can be attached to the skin in an optimal manner, by means of a suitable elastic fastening band structure, for example. In ladies' swimsuits the capsule could also be placed into a pocket provided at the chest. Similarly, the required capsule pocket would be easy to provide in a wet suit.

The measurement electrodes 300, 502, 504 can be made of conductive plastic. Such measurement electrodes 300, 502, 504 can be conveniently integrated as a part of the cover encapsulating the ECG electrode structure. As regards the method of manufacture, the integration can be implemented by manufacturing the cover by injection moulding.

Figure 4:
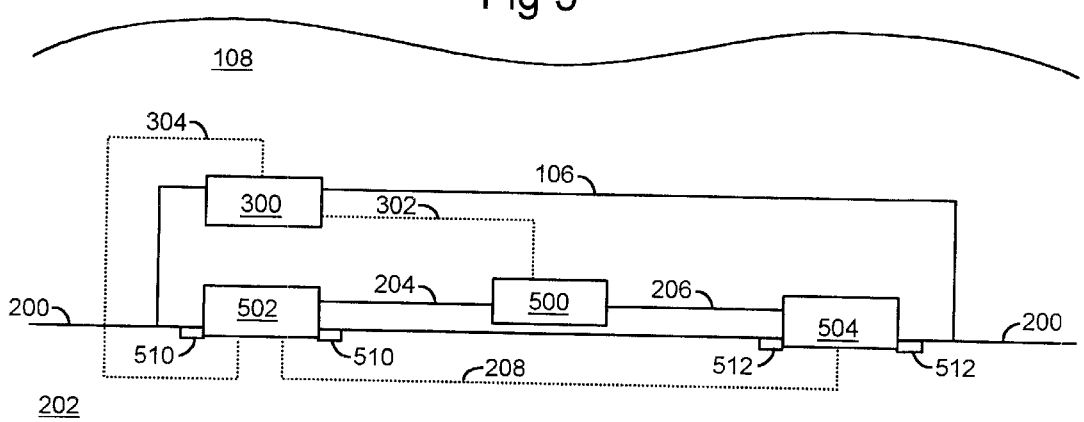
FIG. 4 illustrates a second preferred embodiment of an ECG electrode structure and measurement connections thereof.

FIG. 4 illustrates a second embodiment which is in a way a combination of the prior art described in FIG. 2 and the first embodiment described in FIG. 3. The second embodiment thus comprises one first measurement electrode 502 electrically insulated 510 from the water 108, but two other measurement electrodes. The second measurement electrode 300 only is in contact with the water 108, a third measurement electrode 504 being arranged such that, when in use, it is in contact with an area of the skin 202 on the user's body.

The ECG electrode structure of the second embodiment can be used both when in water and out of it. As shown in FIG. 4, two separate potential differences to be measured may appear between the electrodes. In practice, the potential difference 304 between the second measurement electrode 300 and the first measurement electrode 502 appears only when the ECG electrode structure is in the water. Correspondingly, a potential difference 208 between the third measurement electrode 504 and the first measurement electrode 502 can be detected in principle both when the ECG electrode structure is in the water and when it is out of it, i.e. in the air. In other words, it must be possible to select whether the measurement will be made using the measurement electrode pair 300/502 or the pair 502/504. The decision may be based on measurements where an extremely low current, such as 50 nanoamperes, is connected through the measurement electrode pair and the voltage between the measurement electrode pairs is measured. The measured voltage divided by the current used yields the impedance between the measurement electrodes. The impedance shows whether a measurement needs to be activated or whether the ECG electrode structure is in the water or out of it.

According to the example shown in FIG. 4, if the impedance between the first electrode 502 and the third electrode 504 is less than one megaohm, the measurement is initiated. If the impedance between the first electrode 502 and the second electrode 300 is measured and the value obtained is less than one megaohm, the ECG electrode structure can be concluded to be in the water. The control electronics 500 thus comprise means 602 for measuring both a first impedance between the second measurement electrode 300 and the first measurement electrode 502 and a second impedance between the third measurement electrode 504 and the first measurement electrode 502. In addition, the control electronics 500 comprise means 602 for concluding, on the basis of the measured first and second impedances, whether the user of the ECG electrode structure is in the water or out of it, and for selecting the second measurement electrode 300 for use in the measurement, in addition to the first measurement electrode 502, when the user is in the water, and the third measurement electrode 504 when he is out of it. The necessary means are located in a control part 602 that is in the electronics unit 500, the control part being preferably implemented using a general-purpose microprocessor provided with the necessary system and application software, although diverse hardware implementations are also possible, such as a circuit built of separate logic components, or one or more ASICs (Application Specific Integrated Circuit).

According to the example in FIG. 3, if the impedance between the first electrode 502 and the second electrode 300 is less than one megaohm, a measurement is initiated.

When a measurement to be performed in the air has already been initiated, either manually or automatically, using a method based on the above described impedance calculation, for example, there is also another alternative for selecting the measurement electrode pair to be used in the measurement. In that case the control part 602 comprises means for measuring the potential difference between the first electrode 502 and the second electrode 300 and for concluding, on the basis of the measurement, whether the ECG electrode structure is in the water or in the air, and for selecting the second measurement electrode 300 for use in the measurement, in addition to the first measurement electrode 502, when the structure is in the water and the third measurement electrode 504 when the structure is in the air. When the structure is in the water, an ECG signal between the first electrode 502 and the second electrode 300 is detected, but when the structure is in the air, the ECG signal is not detected.

The above described embodiments relate to cases where the transmitter 606 inside the ECG electrode structure is arranged to use telemetry to transmit heart rate information to the heart rate receiver 104 for display and/or storage and/or further analysis. Another possible embodiment is one where no separate heart rate receiver 104 is needed at all, or the user may use one when he so wishes. In that case the ECG electrode structure comprises a display 638 for displaying the heart rate information. This is described in connection with the first embodiment shown in FIG. 3, but a display integrated in the ECG electrode structure can also be implemented in connection with the second embodiment shown in FIG. 4. The display 638 is connected to the electronics unit 500. If the ECG electrode structure supports the use of a separate heart rate receiver 104 as well, the structure of the electrode structure corresponds to that shown in FIG. 6, otherwise there is no transmitter 606. In one embodiment, the display 638 is a LED display of at least one LED. In another embodiment, the display 638 comprises LEDs of different colours, for example a yellow and/or green and/or red LED. These LEDs can be used to build a more or less complete set of "traffic lights". If the display 638 comprises a yellow LED, it may be used to indicate that the measured variable is below the target range. If the display 638 comprises a green LED, it indicates that the measured variable is within the target range. If the display 638 comprises a red LED, it indicates that the measured variable is above the target range. In a heart rate monitor, for example, heart rate limits such as 140 and 160 may be used. Consequently, at a heart rate between 140 and 160, the green LED would be illuminated, at a heart rate below 140, the yellow LED would be illuminated, and at a heart rate exceeding 160, the red LED would be illuminated. LEDs of other colours may naturally be used as well.

Figure 7:
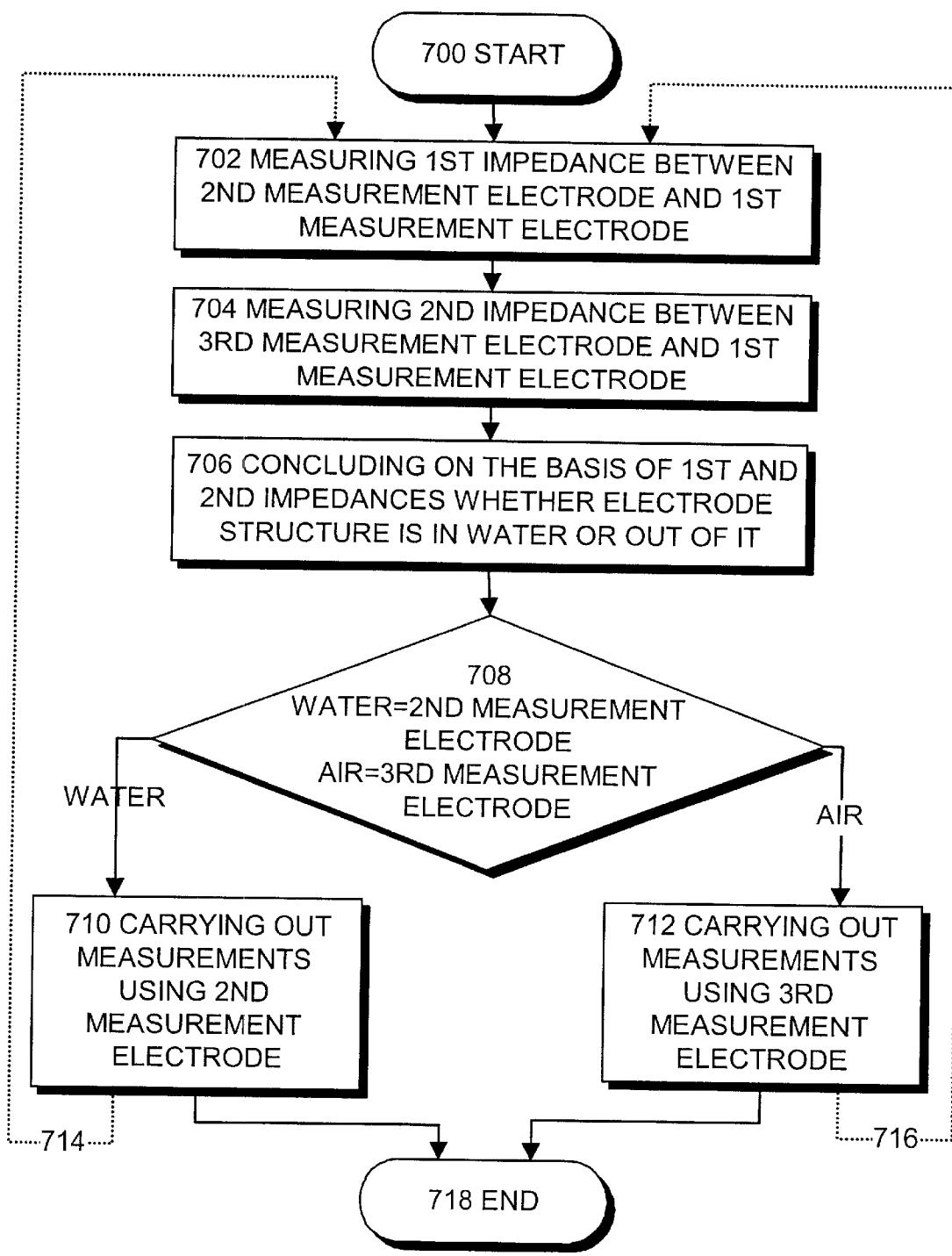
FIG. 7 is a flow diagram illustrating a method for measuring an ECG signal from a person who is in water.

The flow diagram of FIG. 7 illustrates measures to be taken in the method for measuring an ECG signal from a person who is in water. The execution of the method starts in block 700, and in practice it involves carrying out measures related to the initiation of the measurement. In block 710, the voltage between the second measurement electrode 300 and the first measurement electrode 502 is measured in the above-described manner. The first measurement electrode 502 has been arranged to be in contact with an area of the skin 202 on a person's body such that the electrode is electrically insulated from the water 108. The second measurement electrode 300 is arranged to be only in contact with the water 108, the second measurement electrode 300 thus being in contact through the water with an area of the person's body other than the area under the first measurement electrode 502. The above measures allow an ECG signal to be measured from a person who is in water.

When a measurement is to be initiated, or measurement electrodes are to be selected, the routine described above can be executed in block 702 to measure the impedance between the second measurement electrode 300 and the first measurement electrode 502. In block 704 is then measured the voltage between the third measurement electrode 504 and the first measurement electrode 502. The third measurement electrode 504 has been placed in contact with an area of the skin 200 on the person's body.

In block 706 is concluded, on the basis of the first and the second impedances, whether the ECG electrode structure is in the water or out of it. On the basis of this, in block 708 is then selected whether the measurement electrode pair 300/502 or 502/504 will be used in the measurement. If the ECG electrode structure is in the water, the second measurement electrode 300 is selected, and if the ECG electrode structure is in the air, the third measurement electrode 504 is selected. Based on the selection, measurements are then carried out either in block 710 using the second measurement electrode 300 or in block 712 using the third ground electrode 504. The measurement is completed in block 718. Arrows 714 and 716 illustrate a return to measurements carried out using both the measurement electrodes 300, 504 to allow the better one of the measurement electrodes to be selected. The transition 714, 716 could be carried out after a shorter or longer period of time, and in an extreme case very frequently; after every measured pulse even. This would allow to detect very rapidly when the swimmer comes out of the water.

If the measurement has already been initiated, the above described routine can be executed for measuring the potential difference between the first electrode 502 and the second electrode 300, the measurement then allowing to conclude whether the ECG electrode structure is in the water or in the air, and to select either the second measurement electrode 300 for measurement in the water or the third measurement electrode 504 for measurement in the air, in addition to the first measurement electrode 502.

Although the invention is described above with reference to an example according to the accompanying drawings, it is apparent that the invention is not restricted to it, but may vary in many ways within the inventive idea disclosed in the claims.

What is claimed is:

1. An ECG electrode structure for measuring a difference in potential, the structure comprising
    a first measurement electrode arranged to be in contact with an area of the skin on a user's body such that, when in use, the electrode is electrically insulated from water, and
    a second measurement electrode, which, when in use, is arranged to be in contact only with the water, the second measurement electrode thus being in contact through the water to some other area of the person's body than the area under the first measurement electrode.

2. An ECG electrode structure according to claim 1, wherein the first measurement electrode and the second measurement electrode on a cover encapsulating the electrode structure are arranged on cover surface sides facing away from each other.

3. An ECG electrode structure according to claim 1, comprising an ECG detection block inside a cover encapsulating the ECG electrode structure for producing heart rate information on the basis of ECG signal measurements carried out by the measurement electrodes.

4. An ECG electrode structure according to claim 1, comprising a transmitter inside a cover encapsulating the ECG electrode structure.

5. An ECG electrode structure according to claim 4, wherein the transmitter is arranged to use telemetry to transmit heart rate information to a separate heart rate receiver for at least one of display, storage, and further analysis.

6. An ECG electrode structure according to claim 1, comprising a display for displaying heart rate information.

7. An ECG electrode structure according to claim 6, wherein the display is a LED display comprising at least one LED.

8. An ECG electrode structure according to claim 7, wherein the display comprises LEDs of different colours.

9. An ECG electrode structure according to claim 1, comprising a third measurement electrode which, when in use, is arranged to be placed in contact with an area of the skin on the user's body.

10. An ECG electrode structure according to claim 9 comprising means for measuring both a first impedance between the second measurement electrode and the first measurement electrode and a second impedance between the third measurement electrode and the first measurement electrode.

11. An ECG electrode structure according to claim 10 comprising means for concluding, on the basis of the measured first and second impedances, whether the ECG electrode structure is in the water or in the air, and for selecting the second measurement electrode for measurement in the water and the third measurement electrode for measurement in the air, in addition to the first measurement electrode.

12. An ECG electrode structure according to claim 9 comprising means for measuring a potential difference between the first electrode and the second electrode, for concluding, on the basis of the measurement, whether the ECG electrode structure is in the water or in the air, and for selecting the second measurement electrode for measurement in the water and the third measurement electrode for measurement in the air, in addition to the first measurement electrode.

13. An ECG electrode structure according to claim 1, wherein the measurement electrode is made of conductive plastic.

14. An ECG electrode structure according to claim 1, wherein the measurement electrodes are integrated to form a part of a cover encapsulating the ECG electrode structure.

15. An ECG electrode structure according to claim 1 wherein a cover encapsulating the ECG electrode structure is made by injection moulding.

16. A method for measuring an ECG signal from a person who is in water, the method comprising measuring a difference in potential between a second measurement electrode and a first measurement electrode placed in contact with an area of the skin on the person's body such that, when in use, it is electrically insulated from the water, wherein the second measurement electrode is arranged to be in contact only with the water, the second measurement electrode thus being in contact through the water to some other area of the person's body than the area under the first measurement electrode.

17. A method according to claim 16, wherein a third measurement electrode is used, the electrode being arranged in contact with an area of the skin on the person's body.

18. A method according to claim 17, wherein both a first impedance between the second measurement electrode and the first measurement electrode is measured and a second impedance between the third measurement electrode and the first measurement electrode is measured.

19. A method according to claim 18, the method comprising concluding, on the basis of the measured first and second impedances, whether the measurement electrodes are in the water or in the air, and selecting the second measurement electrode for measurement in the water and the third measurement electrode for measurement in the air, in addition to the first measurement electrode.

20. A method according to claim 16, the method comprising measuring a potential difference between the first electrode and the second electrode and concluding, on the basis of the measurement, whether the measurement electrodes are in the water or in the air, and selecting the second measurement electrode for measurement in the water and the third measurement electrode for measurement in the air, in addition to the first measurement electrode.

21. A method according to claim 16, the method comprising producing heart rate information on the basis of ECG signal measurement carried out by the measurement electrodes.

22. A method according to claim 16, the method comprising using telemetry to transmit heart rate information to a separate heart rate receiver for at least one of display, storage, and further analysis.

23. A method according to claim 16, wherein a display connected to the measurement electrodes is used for displaying heart rate information.

24. A method according to claim 23, wherein the display is a LED display comprising at least one LED.

25. A method according to claim 24, wherein the display comprises LEDs of different colours.

* * * * *

UNITED STATES PATENT AND TRADEMARK OFFICE
CERTIFICATE OF CORRECTION

PATENT NO. : 6,580,943 B2
DATED : June 17, 2003
INVENTOR(S) : Nissilä

It is certified that error appears in the above-identified patent and that said Letters Patent is hereby corrected as shown below:

<u>Title page,</u>
Item [74], *Attorney, Agent, or Firm,* now reads "Hoffman & Baron, LLP" should read -- Hoffmann & Baron, LLP --;
Item [57], ABSTRACT,
Line 8, now reads "electrically insulted" should read -- electrically insulated --;

<u>Column 2,</u>
Line 51, now reads "described of example" should read -- described by way of example --.

Signed and Sealed this

Fourth Day of November, 2003

JAMES E. ROGAN
*Director of the United States Patent and Trademark Office*